US012611452B2

(12) United States Patent
Tian et al.

(10) Patent No.: US 12,611,452 B2
(45) Date of Patent: Apr. 28, 2026

(54) FOOT-AND-MOUTH DISEASE VIRUS-LIKE PARTICLE ANTIGEN, VACCINE COMPOSITION, PREPARATION METHOD, AND USE THEREOF

(71) Applicant: PULIKE BIOLOGICAL ENGINEERING, INC., Luoyang (CN)

(72) Inventors: Kegong Tian, Luoyang (CN); Wenqiang Pang, Luoyang (CN); Yan Xiao, Luoyang (CN); Xuke Zhang, Luoyang (CN)

(73) Assignee: PULIKE BIOLOGICAL ENGINEERING INC., Luoyang City (CN)

( * ) Notice: Subject to any disclaimer, the term of this patent is extended or adjusted under 35 U.S.C. 154(b) by 727 days.

(21) Appl. No.: 17/996,879

(22) PCT Filed: Aug. 28, 2020

(86) PCT No.: PCT/CN2020/112115

§ 371 (c)(1),
(2) Date: Oct. 21, 2022

(87) PCT Pub. No.: WO2021/217982

PCT Pub. Date: Nov. 4, 2021

(65) Prior Publication Data

US 2023/0149529 A1 May 18, 2023

(30) Foreign Application Priority Data

Apr. 29, 2020 (CN) .......................... 202010357569.9

(51) Int. Cl.
*C12N 7/00* (2006.01)
*A61K 39/135* (2006.01)
*C12N 15/86* (2006.01)
*A61K 39/00* (2006.01)

(52) U.S. Cl.
CPC ........... *A61K 39/135* (2013.01); *C12N 15/86* (2013.01); *A61K 2039/5258* (2013.01); *A61K 2039/55577* (2013.01); *C12N 2770/32122* (2013.01); *C12N 2770/32123* (2013.01); *C12N 2770/32134* (2013.01)

(58) Field of Classification Search
None
See application file for complete search history.

(56) References Cited

U.S. PATENT DOCUMENTS 2,909,462 A    10/1959   Warfield et al.

FOREIGN PATENT DOCUMENTS

| CN | 105418738 A | | 3/2016 | |
| CN | 105535957 A | * | 5/2016 | ............. A61K 39/39 |
| CN | 106148290 A | | 11/2016 | |
| CN | 106540248 A | | 3/2017 | |
| KR | 20150003948 A | | 1/2015 | |

OTHER PUBLICATIONS

WIPO translation of CN105535957A (Year: 2016).*
Hunter et al., The Theory and Practical Application of Adjuvants (Ed. Stewart-Tull, D. E. S). John Wiley and Sons, NY, pp. 51-94 (1995).
Todd et al. Vaccine 15:564-570 (1997).
Vaccine Design, "The Subunit and Adjuvant Approach" edited by M. Powell and M. Newman, Plenum Press, 1995.

* cited by examiner

*Primary Examiner* — M Franco G Salvoza
(74) *Attorney, Agent, or Firm* — Shumaker, Loop & Kendrick, LLP; John A. Miller

(57) ABSTRACT

The present disclosure provides a type A foot-and-mouth disease virus-like particle antigen assembled by VP2, VP3 and VP1 antigen proteins of an epidemic strain of type A foot-and-mouth disease virus. The type A foot-and-mouth disease virus VP2 antigen protein is encoded by a nucleotide sequence shown in SEQ ID No. 1 or its degenerate sequence, the type A foot-and-mouth disease virus VP3 antigen protein is encoded by a nucleotide sequence shown in SEQ ID No. 2 or its degenerate sequence, and the type A foot-and-mouth disease virus VP1 antigen protein is encoded by a nucleotide sequence shown in SEQ ID No. 3 or its degenerate sequence.

14 Claims, No Drawings
Specification includes a Sequence Listing.

SEQUENCE LISTING

```
<160> NUMBER OF SEQ ID NOS: 10

<210> SEQ ID NO 1
<211> LENGTH: 654
<212> TYPE: DNA
<213> ORGANISM: Artificial Sequence
<220> FEATURE:
<223> OTHER INFORMATION: Synthetic Sequence

<400> SEQUENCE: 1
gacaaaaaaa ccgaagaaac caccctgctg gaagaccgta tcctgaccac ccgtaacggt        60
cacaccacct ctaccaccca gtcttctgtt ggtgttacct gcggttactc taccggtgaa       120
gaccacgttt ctggtccgaa cacctctggt ctggaaaccc gtgttgttca ggctgaacgt       180
```

```
ttcttcaaaa aacacctgtt cgactggacc accgacaaac cgttcggtca caccgaaaaa      240
ctggaactgc cgaccgaaca caaaggtgtt tacggtcagc tggttgaatc tttcgcttac      300
atgcgtaacg gttgggacgt tgaagtttct gctgttggta accagttcaa cggtggttgc      360
ctgctggttg ctatggttcc ggaattcaaa gaattcaccc agcgtgaaaa ataccagctg      420
accctgttcc cgcaccagtt catctctccg cgtaccaaca tgaccgctca catcaccgtt      480
ccgtacctgg gtgttaaccg ttacgaccag tacaaaaaac acaaaccgtg gaccctggtt      540
gttatggttg tttctccgct gaccacctct tctatcggtg ctacccagat caaagtttac      600
gctaacatcg ctccgaccca cgttcacgtt gctggtgaac tgccgtctaa agaa           654

<210> SEQ ID NO 2
<211> LENGTH: 663
<212> TYPE: DNA
<213> ORGANISM: Artificial Sequence
<220> FEATURE:
<223> OTHER INFORMATION: Synthetic Sequence

<400> SEQUENCE: 2
ggtatcgttc cggttgcttg ctctgacggt tacggtggtc tggttaccac cgacccgaaa       60
accgctgacc cggcttacgg tatggtttac aacccgccgc gtaccaacta cccgggtcgt      120
ttcaccaacc tgctggacgt tgctgaagct tgcccgacct tcctgtgctt cgacgacggt      180
aaaccgtaca tcgttacccg taccgacgaa cagcgtctgc tggctaaatt cgacctgtct      240
ctggctgcta aacacatgtc taacacctac ctgtctggta tcgctcagta ctacgctcag      300
tactctggta ccatcaacct gcacttcatg ttcaccggtt ctaccgactc taaagctcgt      360
tacatggttg cttacgttcc gccgggtgct gaaaccccgc cggacacccc ggaaaaagct      420
gctcactgca tccacgctga atgggacacc ggtctgaact ctaaattcac cttctctatc      480
ccgtacgttt ctgctgctga ctacgcttac accgcttctg acgaagctga aaccaccaac      540
gttcagggtt gggtttgcat ctaccagatc acccacggta aagctgaaca ggacaccctg      600
gttgtttctg tttctgctgg taaagacttc gaactgcgtc tgccgatcga cccgcgtgct      660
cag                                                                     663

<210> SEQ ID NO 3
<211> LENGTH: 636
<212> TYPE: DNA
<213> ORGANISM: Artificial Sequence
<220> FEATURE:
<223> OTHER INFORMATION: Synthetic Sequence

<400> SEQUENCE: 3
accaccgcta ccggtgaatc tgctgacccg gttaccacca ccgttgaaaa ctacggtggt       60
gaaacccagg ttcagcgtcg ttaccacacc gacgttggtt tcctgatgga ccgtttcgtt      120
cagatcaaac cggttggtcc gacccacgtt atcgacctga tgcagaccca ccagcacggt      180
ctggttggtg ctatgctgcg tgctgctacc tactacttct ctgacctgga aatcgttgtt      240
aaccacaccg gtaacctgac ctgggttccg aacggtgctc cggaagctgc tctgcagaac      300
acctctaacc cgaccgctta ccacaaagct ccgttcaccc gtctggctct gccgtacacc      360
gctccgcacc gtgttctggc taccgtttac tctggtacct ctaaatactc tgctccgcag      420
aaccgtcgtg gtgactctgg tccgctggct gctcgtctgg ctgctcagct gccggcttct      480
ttcaacttcg gtgctatccg tgctaccgaa atccgtgaac tgctggttcg tatgaaacgt      540
gctgaactgt actgcccgcg tccgctgctg ctgttgaag tttcttctca ggaccgtcac       600
```

```
aaacagaaaa tcatcgctcc ggctaaacag ctgctg                                636
```

```
<210> SEQ ID NO 4
<211> LENGTH: 255
<212> TYPE: DNA
<213> ORGANISM: Artificial Sequence
<220> FEATURE:
<223> OTHER INFORMATION: Synthetic Sequence

<400> SEQUENCE: 4
ggtgctggtc agtcttctcc ggctaccggt tctcagaacc agtctggtaa caccggttct     60
atcatcaaca actactacat gcagcagtac cagaactcta tggacaccca gctgggtgac    120
aacgctatct ctggtggttc taacgaaggt tctaccgaca ccacctctac ccacaccacc    180
aacacccaga acaacgactg gttctctaaa ctggcttctt ctgctttctc tggtctgttc    240
ggtgctctgc tggct                                                     255
```

```
<210> SEQ ID NO 5
<211> LENGTH: 654
<212> TYPE: DNA
<213> ORGANISM: Artificial Sequence
<220> FEATURE:
<223> OTHER INFORMATION: Synthetic Sequence

<400> SEQUENCE: 5
gacaaaaaaa ccgaagaaac caccctgctg gaagaccgta tcctgaccac ccgtaacggt     60
cacaccacct ctaccaccca gtcttctgtt ggtatcaccc acggttacgc taccgctgaa    120
gacttcgttt ctggtccgaa cacctctggt ctggaaaccc gtgttatcca ggctgaacgt    180
ttcttcaaaa cccacctgtt cgactgggtt acctctgacc cgttcggtcg ttaccacctg    240
ctggaactgc cgaccgacca caaaggtgtt tacggttctc tgaccgactc ttacgcttac    300
atgcgtaacg gttgggacgt tgaagttacc gctgttggta accagttcaa cggtggttgc    360
ctgctggttg ctatggttcc ggaactgtgc tctatcgaac gtcgtgaact gttccagctg    420
accctgttcc cgcaccagtt catcaacccg cgtaccaaca tgaccgctca catcaaagtt    480
ccgttcgttg gtgttaaccg ttacgaccag tacaaagttc acaaaccgtg gaccctggtt    540
gttatggttg ttgctccgct gaccgttaac accgaaggtg ctccgcagat caaagtttac    600
gctaacatcg ctccgaccaa cgttcacgtt gctggtgaat tcccgtctaa agaa          654
```

```
<210> SEQ ID NO 6
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 6
ggtatcttcc cggttgcttg ctctgacggt tacggtggtc tggttaccac cgacccgaaa     60
accgctgacc cggtttacgg taaagttttc aacccgccgc gtaacatgct gccgggtcgt    120
ttcaccaacc tgctggacgt tgctgaagct tgcccgacct tcctgcactt cgacggtgac    180
gttccgtacg ttaccaccaa aaccgactct gaccgtgttc tggctcagtt cgacctgtct    240
ctggctgcta acacatgtc taacaccttc ctggctggtc tggctcagta ctacacccag    300
tactctggta ccatcaacct gcacttcatg ttcaccggtc cgaccgacgc taaagctcgt    360
tacatgatcg cttacgctcc gccgggtatg gaaccgccga aaaccccgga agctgctgct    420
```

-continued

```
cactgcatcc acgctgaatg ggacaccggt ctgaactcta aattcacctt ctctatcccg        480
tacctgtctg ctgctgacta cgcttacacc gcttctggtg ctgctgaaac caccaacgtt        540
cagggttggg tttgcctgtt ccagatcacc cacggtaaag ctgaaggtga cgctctggtt        600
gttctggctt ctgctggtaa agacttcgaa ctgcgtctgc cggttgacgc tcgtcagcag        660

<210> SEQ ID NO 7
<211> LENGTH: 639
<212> TYPE: DNA
<213> ORGANISM: Artificial Sequence
<220> FEATURE:
<223> OTHER INFORMATION: Synthetic Sequence

<400> SEQUENCE: 7
accacctcta ccggtgaatc tgctgacccg gttaccgcta ccgttgaaaa ctacggtggt         60
gaaacccagg ttcagcgtcg tcaccacacc gacgtttctt tcatcctgga ccgtttcgtt        120
aaagttaccc cgaaagactc tatcaacgtt ctggacctga tgcagacccc gccgcacacc        180
ctggttggtg ctctgctgcg taccgctacc tactacttcg ctgacctgga agttgctgtt        240
aaacacaaag gtgacctgac ctgggttccg aacggtgctc cggaagctgc tctggacaac        300
accaccaacc cgaccgctta ccacaaagct ccgctgaccc gtctggctct gccgtacacc        360
gctccgcacc gtgttctggc taccgtttac aacggtaact gcaaatacgc tggtggttct        420
ctgccgaacg ttcgtggtga cctgcaggtt ctggctcaga aagctgcttg ccgctgccg        480 acctctttca actacggtgc tatcaaagct acccgtgtta ccgaactgct gtaccgtatg        540
aaacgtgcta aacctactg cccgcgtccg ctgctggctg ttcacccgtc tgctgctcgt        600
cacaaacaga aaatcgttgc tccggttaaa cagtctctg                                639

<210> SEQ ID NO 8
<211> LENGTH: 909
<212> TYPE: DNA
<213> ORGANISM: Artificial Sequence
<220> FEATURE:
<223> OTHER INFORMATION: Synthetic Sequence

<400> SEQUENCE: 8
ggtgctggtc agtcttctcc gaccaccggt tctcagaacc agtctggtaa caccggttct         60
atcatcaaca actactacat gcagcagtac cagaactcta tggacaccca gctgggtgac        120
aacgctatct ctggtggttc taacgaaggt tctaccgaca ccacctctac ccacaccaac        180
aacacccaga caacgactg gttctctaaa ctggctaaca ccgctttctc tggtctgttc        240
ggtgctctgc tggctgacaa aaaaaccgaa gaaaccaccc tgctggaaga ccgtatcctg        300
accacccgta cggtcacac cacctctacc acccagtctt ctgttggtgt tacctacggt        360
tacgctaccg ctgaagactt cgtttctggt ccgaacacct ctggtctgga aacccgtgtt        420
gttcaggctg aacgtttctt caaaacccac ctgttcgact ggggtaccaa cgactctttc        480
ggtcgttgcc acctgctgga actgccgacc gaccacaaag gtgtttacgg ttctctgacc        540
gactcttacg cttacatgcg taacggttgg gacgttgaag ttaccgctgt tggtaaccag        600
ttcaacggtg gttgcctgct ggttgctatg gttccggaac tgcgttctat caccaaacgt        660
gaactgtacc agctgaccct gttcccgcac cagttcatca cccgcgtac caacatgacc        720 gctcacatca ccgttccgta cctgggtgtt aaccgttacg accagtacaa agttcacaaa        780
ccgtggaccc tggttgttat ggttgttgct ccgctgaccg ttaacaacga aggtgctccg        840
cagatcaaag tttacgctaa catcgctccg accaacgttc acgttgctgg tgaactgccg        900
```

-continued

```
tctaaagaa                                                      909

<210> SEQ ID NO 9
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 9
ggtatcttcc cggttgcttg ctctgacggt tacggtggtc tggttaccac cgacccgaaa     60
accgctgacc cggtttacgg taaagttttc aacccgccgc gtaacctgct gccgggtcgt    120
ttcaccaacc tgctggacgt tgctgaagct tgcccgacct tcctgcactt cgacggtgac    180
gttccgtacg ttgttaccaa aaccgactct gaccgtgttc tggctcagtt cgacctgtct    240
ctggctgcta aacacatgtc taacaccttc ctggctggtc tggctcagta ctacgctcag    300
tactctggta ccatcaacct gcacttcatg ttcaccggtc cgaccgacgc taaagctcgt    360
tacatggttg cttacgctcc gccgggtatg gaaccgccga aaaccccgga agctgctgct    420
cactgcatcc acgctgaatg ggacaccggt ctgaactcta aattcacctt ctctatcccg    480
tacctgtctg ctgctgacta cgcttacacc gcttctgacg ttgctgaaac caccaacgtt    540
cagggttggg tttgcctgtt ccagatcacc cacggtaaag ctgacggtga cgctctggtt    600
gttctggctt ctgctggtaa agacttcgac ctgcgtctgc cggttgacgc tcgtacccag    660

<210> SEQ ID NO 10
<211> LENGTH: 633
<212> TYPE: DNA
<213> ORGANISM: Artificial Sequence
<220> FEATURE:
<223> OTHER INFORMATION: Synthetic Sequence

<400> SEQUENCE: 10
accacctctg ctggtgaatc tgctgacccg gttaccacca ccgttgaaaa ctacggtggt     60
gaaacccagg ttcagcgtcg tcagcacacc gacgttgctt tcatcctgga ccgtttcgtt    120
aaagttaaac cgcaggaaca ggttaacgtt ctggacctga tgcagatccc ggctcacacc    180
ctggttggtg ctctgctgcg taccgctacc tactacttct ctgacctgga actggctgtt    240
aaacacgaag gtgacctgac ctgggttccg aacggtgctc cggaaaccgc tctggacaac    300
accaccaacc cgaccgctta ccacaaagaa ccgctgaccc gtctggctct gccgtacacc    360
gctccgcacc gtgttctggc taccgtttac aacggttctt ctaaatacgg tgacgcttct    420
accaacaacg ttcgtggtga cctgcaggtt ctggttaaaa aagctgaacg tgctctgccg    480
acctctttca actacggtgc tatcaaagct gctcgtgtta ccgaactgct gtaccgtatg    540
aaacgtgctg aaacctactg cccgcgtccg ctgctggcta tccagccgtc taccgctcgt    600
cacaaacaga aatcgttgc tccggctaaa cag                                  633
```

FOOT-AND-MOUTH DISEASE VIRUS-LIKE PARTICLE ANTIGEN, VACCINE COMPOSITION, PREPARATION METHOD, AND USE THEREOF

CROSS REFERENCE TO RELATED APPLICATIONS

This application is a National Stage application of International Application No. PCT/CN2020/112115 filed on Aug. 28, 2020, which claims priority to Chinese Application No. 202010357569.9 filed Apr. 29, 2020.

BACKGROUND

Field

The present disclosure belongs to a viral antigen and a pharmaceutical preparation of the antigen. Specifically, the present disclosure relates to a foot-and-mouth disease virus-like particle antigen, a vaccine composition prepared therefrom, and a preparation method and use thereof.

Discussion of the Related Art

Foot-and-mouth disease (FMD) is an acute, highly contagious animal disease that can quickly spread over long distances and is the most infectious disease for mammals, among which infection in cloven-hoofed animals will cause significant economic losses globally. Animals suffering from foot-and-mouth disease include cattle, sheep and swine. A pathogenic factor is Foot-and-Mouth Disease Virus (FMDV), which is an aphthovirus belonging to the picornavirus family. The virus has 7 serotypes (types A, O, C, Asia, SAT1, SAT2 and SAT3), among which type O foot-and-mouth disease virus and type A foot-and-mouth disease virus are most prevalent in China. Vaccination is an effective measure to control this disease and protect livestock from harm.

With the continuous spread of type A foot-and-mouth disease, the type A foot-and-mouth disease virus in China has undergone great changes. In the course of natural epidemics, type A foot-and-mouth disease virus mainly causes infection and illness in cattle and sheep and rarely in swine. However, unlike in the past, the currently prevalent type A foot-and-mouth disease virus is pathogenic to cattle and swine, which is 10-times more virulent than the previous type A virus. There is a lack of a vaccine with advantages in biological safety and immune effect on the market.

Virus-like particles (VLPs) are particles similar to viruses, that can self assemble into virus shell structures when expressed in vitro and/or in vivo, and pseudoviruses that have similar shell structures of viruses but do not have the ability to replicate. VLPs vaccine can effectively stimulate the body to produce anti-infection and anti-tumor immunity. A vaccine based on virus-like particles is an ideal form of vaccine. Therefore, it is an urgent task to screen out ideal sequences of foot-and-mouth disease strain to prepare virus-like particles which also meets the needs of the country to effectively prevent and control major animal diseases and ensure healthy and sustainable development of animal husbandry.

SUMMARY

In order to solve the problem of type A foot-and-mouth disease virus epidemic strains in the prior art, the present disclosure provides a type A foot-and-mouth disease virus-like particle antigen, wherein the type A foot-and-mouth disease virus-like particle antigen is assembled by VP2, VP3 and VP1 antigen proteins of an epidemic strain of type A foot-and-mouth disease virus, the type A foot-and-mouth disease virus VP2 antigen protein is encoded by a nucleotide sequence shown in SEQ ID No. 1 or its degenerate sequence, the type A foot-and-mouth disease virus VP3 antigen protein is encoded by a nucleotide sequence shown in SEQ ID No. 2 or its degenerate sequence, and the type A foot-and-mouth disease virus VP1 antigen protein is encoded by a nucleotide sequence shown in SEQ ID No. 3 or its degenerate sequence.

The foot-and-mouth disease virus-like particle antigen has good immunogenicity, and a single-shot vaccine composition prepared therefrom can provide complete protection against the type A foot-and-mouth disease virus epidemic strain. Meanwhile, the foot-and-mouth disease virus-like particle antigen has good stability. After being placed at 4° C. for 3 months, it can be observed through the electron microscope after negative staining with phosphotungstic acid that the virus-like particles are still plump without aggregation.

The type A foot-and-mouth disease virus-like particle antigen is derived from a current epidemic strain and can produce complete protection against the current epidemic wild strain.

The present disclosure also provides a vaccine composition, wherein the vaccine composition comprises an immune amount of the type A foot-and-mouth disease virus-like particle antigen and a pharmaceutically acceptable carrier.

The foot-and-mouth disease virus-like particle vaccine of type A epidemic strain of the present disclosure can reach an antibody titer of above 1:128 on the $14^{th}$ day after immunization and mantian long-term high antibody titers which can produce protection for the entire fattening period, even when the antigen content is only 160 µg/ml, demonstrating good immunogenicity.

As an embodiment of the present disclosure, in the vaccine composition of the present disclosure, content of the type A foot-and-mouth disease virus-like particle antigen is 160-240 µg/m.

The content of the type A foot-and-mouth disease virus-like particle antigen can be selected from 160 µg/ml, 170 µg/ml, 180 µg/ml, 190 µg/ml, 200 µg/ml, 210 µg/ml, 220 µg/ml, 230 µg/ml, and 240 µg/ml.

Even when the content of the type A foot-and-mouth disease virus-like particle antigen is only 160 µg/ml, an antibody titer of above 1:128 can be reached on the $14^{th}$ day after immunization, i.e. immune protection can be procured, and long-term high antibody titers can be maintained.

As a preferred embodiment of the present disclosure, in the vaccine composition of the present disclosure, the content of the type A foot-and-mouth disease virus-like particle antigen is 160 µg/ml, 200 µg/ml or 240 µg/ml.

As an embodiment of the present disclosure, in the vaccine composition of the present disclosure, the pharmaceutically acceptable carrier comprises an adjuvant which is selected from one or more of (1) mineral oil, alhydrogel adjuvant, saponins, Avridine, didecyl adipate (DDA); (2) water-in-oil emulsion, oil-in-water emulsion, water-in-oil-in-water emulsion; or (3) polymers of acrylic or methacrylic acid, copolymers of maleic anhydride and alkenyl derivative; and the RIBI adjuvant system, Block co-polymer, SAF-M, monophosphoryl lipid A, Avridine lipid-amine adjuvant, heat-labile enterotoxin from E. coli, cholera toxin, IMS 1314, muramyl dipeptide, Montanide ISA 206 and Gel adjuvant; preferably, the saponin is Quil A, QS-21 or GPI-0100; preferably, the adjuvant is ISA 206 adjuvant.

The content of the adjuvant is 5%-60% V/V, preferably 30%-60% V/V, more preferably 50% V/V.

As an embodiment of the present disclosure, in the vaccine composition of the present disclosure, the vaccine composition further includes an immune amount of type O SEA topotype foot-and-mouth disease virus-like particle antigen and/or an immune amount of type O CATHAY topotype foot-and-mouth disease virus-like particle antigen, wherein the type O SEA topotype foot-and-mouth disease virus-like particle antigen is assembled by VP4, VP2, VP3 and VP1 antigen proteins of an epidemic strain of type O SEA topotype foot-and-mouth disease virus, wherein the type O SEA topotype foot-and-mouth disease virus VP4 antigen protein is encoded by a nucleotide sequence shown in SEQ ID No. 4 or its degenerate sequence, the type O SEA topotype foot-and-mouth disease virus VP2 antigen protein is encoded by a nucleotide sequence shown in SEQ ID No. 5 or its degenerate sequence, the type O SEA topotype foot-and-mouth disease virus VP3 antigen protein is encoded by a nucleotide sequence shown in SEQ ID No. 6 or its degenerate sequence, the type O SEA topotype foot-and-mouth disease virus VP1 antigen protein is encoded by a nucleotide sequence shown in SEQ ID No. 7 or its degenerate sequence; and the type O CATHAY topotype foot-and-mouth disease virus-like particle antigen is assembled by VP0, VP3 and VP1 antigen proteins of type O CATHAY topotype foot-and-mouth disease virus epidemic strains, wherein the type O CATHAY topotype foot-and-mouth disease virus VP0 antigen protein is encoded by a nucleotide sequence shown in SEQ ID No. 8 or its degenerate sequence, the type O CATHAY topotype foot-and-mouth disease virus VP3 antigen protein is encoded by a nucleotide sequence shown in SEQ ID No. 9 or its degenerate sequence, the type O CATHAY topotype foot-and-mouth disease virus VP1 antigen protein is encoded by a nucleotide sequence shown in SEQ ID No. 10 or its degenerate sequence.

The type O SEA topotype foot-and-mouth disease virus-like particle antigen of the present disclosure has good immunogenicity, and an antibody titer of above 1:128 can be reached on the $14^{th}$ day after immunization. The type O SEA topotype foot-and-mouth disease virus-like particle antigen has good stability. After being placed at 4° C. for 3 months, it can be observed through the electron microscope after negative staining with phosphotungstic acid that the virus-like particles are still plump without aggregation.

The type O CATHAY topotype foot-and-mouth disease virus-like particle antigen of the present disclosure has good immunogenicity, and an antibody titer of above 1:128 for the type O CATHAY topotype foot-and-mouth disease virus can be reached on the $14^{th}$ day after immunization. The type O CATHAY topotype foot-and-mouth disease virus-like particle antigen has good stability. After being placed at 4° C. for 3 months, it can be observed through the electron microscope after negative staining with phosphotungstic acid that the virus-like particles are still plump without aggregation.

As a preferred embodiment of the present disclosure, in the vaccine composition of the present disclosure, the content of the type O SEA topotype foot-and-mouth disease virus-like particle antigen is 100-200 µg/ml; the content of the type O CATHAY topotype foot-and-mouth disease virus-like particle antigen is 100-200 µg/ml.

The content of the type O SEA topotype foot-and-mouth disease virus-like particle antigen can be selected from 100

µg/ml, 110 µg/ml, 120 µg/ml, 130 µg/ml, 140 µg/ml, 150 µg/ml, 160 µg/ml, 170 µg/ml, 180 µg/ml, 190 µg/ml and 200 µg/ml.

The type O SEA topotype foot-and-mouth disease virus-like particle antigen can reach an antibody titer of above 1:128 on the $14^{th}$ day after immunization and mantian long-term high antibody titers, even when the antigen content is only 100 µg/ml, demonstrating good immunogenicity.

The content of the type O CATHAY topotype foot-and-mouth disease virus-like particle antigen can be selected from 100 µg/ml, 110 µg/ml, 120 µg/ml, 130 µg/ml, 140 µg/ml, 150 µg/ml, 160 µg/ml, 170 µg/ml, 180 µg/ml, 190 µg/ml and 200 µg/ml.

The type O CATHAY topotype foot-and-mouth disease virus-like particle antigen can reach an antibody titer of above 1:128 on the 14th day after immunization and mantian long-term high antibody titers, even when the antigen content is only 100 µg/ml, demonstrating good immunogenicity.

In the vaccine composition of the present disclosure containing type A foot-and-mouth disease virus-like particle antigen, type O SEA topotype foot-and-mouth disease virus-like particle antigen and type O CATHAY topotype foot-and-mouth disease virus-like particle antigen, the two types of type O foot-and-mouth disease virus-like particle antigens synergistically enhance the immune effect, and even if the contents of the antigens are reduced by half, the immune effect of the single vaccine of each component can be exerted.

As a more preferred embodiment of the present disclosure, in the vaccine composition of the present disclosure, the content of the type O SEA topotype foot-and-mouth disease virus-like particle antigen is 100 µg/ml, 150 µg/ml, or 200 µg/ml; and the content of the type O CATHAY topotype foot-and-mouth disease virus-like particle antigen is 100 µg/ml, 150 µg/ml, or 200 µg/ml.

As an embodiment of the present disclosure, the pharmaceutically acceptable carrier includes drugs, immunostimulants, antioxidants, surfactants, colorants, volatile oils, buffers, dispersants, propellants and preservatives; the immunostimulants include α-interferon, β-interferon, γ-interferon, granulocyte-macrophage colony stimulating factor (GM-CSF), macrophage colony stimulating factor (M-CSF) and interleukin 2 (IL2).

To prepare such a composition, methods known in the art can be used.

The present disclosure also relates to a method for preparing the vaccine composition, wherein the method comprises: step (1) cloning and recombining genes of VP2, VP3, VP1 antigen proteins of the type A foot-and-mouth disease virus respectively into a common tandem expression vector; step (2) transforming or transducing a host cell with the recombinant expression vector obtained in the step (1) and solubly expressing recombinant SUMO-VP2 antigen protein, recombinant SUMO-VP3 antigen protein and recombinant SUMO-VP1 antigen protein of type A foot-and-mouth disease virus which can self-assemble to form virus-like particle antigens; Step (3) separating and purifying the recombinant antigens of type A foot-and-mouth disease virus obtained in the step (2) and removing SUMO fusion tags through digestion and purification; and step (4) self-assembling to virus-like particle antigens, then adding an adjuvant to obtain the vaccine composition. The present disclosure can obtain stable self-assembled virus-like particles by expressing the VP2, VP3, and VP1 antigen proteins of type A foot-and-mouth disease virus epidemic strain and facilitate subsequent purification and separation of antigens by expressing in tandem the VP2, VP3, and VP1 antigen proteins of type A foot-and-mouth disease virus epidemic strain. The expressed and purified active protein can efficiently self-assemble into a type A epidemic strain foot-and-mouth disease virus-like particle antigen.

As an embodiment of the present disclosure, in the method of the present disclosure, the tandem expression vector in step (1) is pET28a, pET28b or pET32a; the host cell in step (2) is E. coli BL21 (DE3), Origami B(DE3) pLysS, or Rosetta-gami B(DE3).

In the present disclosure, the VP2, VP3, and VP1 antigen proteins are expressed in tandem by selecting the tandem expression vector and the host bacteria, which facilitates subsequent antigen separation and purification and simplifies the procedure. The soluble proteins expressed, purified and self-assembled into virus-like particles have biological activity.

As a preferred embodiment of the present disclosure, in the method of the present disclosure, in the step (2), after the host cell is amplified, IPTG is added to induce expression of the protein.

As a preferred embodiment of the present disclosure, in the method of the present disclosure, the separating and purifying process of step (3) is broking the bacterial cells, retaining the supernatant, and purifying the virus-like particle antigen by ammonium sulfate fractional precipitation and chromatography.

In the present disclosure, the three structural proteins VP2, VP3, and VP1 of type A foot-and-mouth disease virus is used for the first time to produce foot-and-mouth disease virus-like particles, which has the advantages such as good immunogenicity, and no bio-safety risks etc. The virus-like particle vaccine composition prepared in the present disclosure can not only provide protective activity against type A foot-and-mouth disease, but also produces high levels of antibodies quickly, significantly increase duration of immunity and maintain immune protection for a long time.

The present disclosure also relates to use of the vaccine composition in preparation of medicaments for preventing and/or treating type A foot-and-mouth disease.

The subject of administration of the medicaments for preventing and/or treating foot-and-mouth disease virus infection of the present disclosure includes swine.

The vaccine composition of the present disclosure can maintain an antibody titer of more than 1:128 for up to 133 days after a single-shot vaccination, and produce complete protection to swine for a long period which can cover the entire fattening period.

DETAILED DESCRIPTION OF THE EMBODIMENTS

Hereinafter, embodiments of the present disclosure will be described.

"Foot-and-mouth disease virus" belongs to Aphthovirus genus of the Picornaviridae family. The virus is classified into seven serotypes, O, A, C, SAT1, SAT2, SAT3 (that is, Southern African Territories 1, 2, 3) and Asia 1, between each of which there is no cross-protection reaction, and there are multiple subtypes within each serotype. At the center of the virus is a single strand of positive-sense RNA consisting of about 8000 bases, which is the basis of infection and heredity, surrounded by proteins which determines antigenicity, immunity and serological response of the virus; the capsid of the virus is a symmetrical icosahedron. Foot-and-mouth disease virus is the pathogen of foot-and-mouth disease, a highly contagious disease of cloven-hoofed animals. The disease ranks as first in the list 'A' of infectious diseases of animals according to the Office International des Epizooties (OIE) and listed as List A disease in the List of Quarantine Disease for the Animals Imported to the People's Republic of China. Prevention and treatment of foot-and-mouth disease in China is mainly through vaccination, and once infected with foot-and-mouth disease, animals will be killed.

"Antigen" refers to a substance that can induce an immune response in the body, that is, it can be specifically recognized and bound by the antigen receptor (TCR/BCR) on the surface of T/B lymphocytes to activate T/B cells and make them proliferate, differentiate and produce immune response products (sensitized lymphocytes or antibodies), and can specifically bind to the corresponding products in vivo and in vitro.

"Virus-like particles (VLPs)" are particles assembled from one or more viral structural proteins, which have external structures and antigenicity similar to viral particles, but do not contain viral genes.

"VP2, VP3, VP1 antigen proteins of the foot-and-mouth disease virus": FMDV structural protein precursor protein P1 is catalyzed and processed by protease 3C into VP0, VP1 and VP3. These three proteins self-assemble into an icosahedral viral capsid. VP0 protein is the intermediate of P1 after cleavage by protease 3C. VP2 and VP4 are generated by maturation cleavage of VP0, in the last stage of the formation of the viral particle.

The term "vaccine" or "vaccine composition" as used in the present disclosure refers to a pharmaceutical composition containing foot-and-mouth disease virus-like particle antigens that can induce, stimulate or enhance an immune response of a swine against FMDV.

The term "immune amount" should be understood as an "immunologically effective amount," also refers to an immunoprotective amount or an effective amount to produce an immune response, which is an amount of antigen effective to induce an immune response in a recipient, which immune amount is sufficient to prevent or ameliorate signs or symptoms of a disease including adverse health effects or complications of the disease. The immune response may be sufficient for diagnostic purposes or other tests or may be suitable for use in preventing signs or symptoms of a disease, including adverse health consequences caused by an infection caused by a pathogen, or complications of the disease. Humoral immunity or cell-mediated immunity or both may be induced. The immune response of the animal to the immunogenic composition may be assessed indirectly, for example, by measuring antibody titers and analyzing lymphocyte proliferation, or directly by monitoring signs or symptoms after challenge with wild-type strains, while protective immunity provided by the vaccine may be assessed by measuring, for example, clinical signs of subjects such as mortality, reduction in morbidity, temperature values, and overall physiological condition and overall health and performance of the subjects. The immune response may include, but are not limited to induction of cellular and/or humoral immunity.

The term "pharmaceutically acceptable carrier" refers to all components other than the foot-and-mouth disease virus antigen in the vaccine composition of the present disclosure which are carriers or diluents that do not cause significant irritation to an organism and do not abrogate the biological activity and properties of the administered compounds, preferably an adjuvant. The term "adjuvant" may includes a compound selected from a group consisting of alhydrogel adjuvant, saponins e.g., Quil A. QS-21 (Cambridge Biotech Inc., Cambridge Mass.), GPI-0100 (Galenica Pharmaceuticals, Inc., Birmingham, AL), water-in-oil emulsion, oil-in-water emulsion, water-in-oil-in-water emulsion, the polymers of acrylic or methacrylic acid, and the copolymers of maleic anhydride and alkenyl derivative. The term "emulsion" may be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifier to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxy-stearic acids, which are optionally ethoxylated, and polyoxypropylene-polyoxyethylene block copolymers, in particular the Pluronic products, especially L121. See Hunter et al., The Theory and Practical Application of Adjuvants (Ed. Stewart-Tull, D. E. S). John Wiley and Sons, NY, pp 51-94 (1995) and Todd et al. Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of the same book. The term "polymers of acrylic or methacrylic acid" preferably are the polymers of acrylic or methacrylic acid which are cross-linked, especially with polyalkenyl ethers of sugars or polyalcohols. These compounds are known by the term carbomer (Trade name, Carbopol) (Phameuropa Vol. 8, No. 2, June 1996). Persons skilled in the art can also refer to U.S. Pat. No. 2,909,462 which describes such acrylic polymers cross-linked with a polyhydroxylated compounds having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio. USA) are particularly appropriate. They are cross-linked with an allyl sucrose or with allyl pentaerythritol. Among them, there may be mentioned Carbopol 974P, 934P and 971 P, most preferably Carbopol 971P. For the term "copolymerrs of maleic anhydride and alkenyl derivative", EMA (Monsanto), which is the copolymer of maleic anhydride and ethylene, can also be considered. The dissolution of these polymers in water leads to an acid solution that will be neutralized, preferably to physiological pH, in order to give the adjuvant solution, into which the immunogenic, immunological or vaccine composition itself will be incorporated. The term "adjuvant" includes, but is not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, muramyl dipeptide, and Gel adjuvant among many others. Preferably, the adjuvant includes one or more of white oil, alhydrogel adjuvant, saponins, water-in-oil emulsion, oil-in-water emulsion, water-in-oil-in-water emulsion, the polymers of acrylic or methacrylic acid, the copolymers of maleic anhydride and alkenyl derivative, the RIBI adjuvant system, Block copolymer, SAF-M, monophosphoryl lipid A, Avridine lipid-amine adjuvant, heat-labile enterotoxin from *E. coli*, cholera toxin, IMS 1314, muramyl dipeptide, Montanide ISA 206 and Gel adjuvant.

"Degenerate sequence": in molecular biology, the phenomenon that a common amino acid has two or more codons is called degeneracy of codon, and such a sequence is called a degenerate sequence.

"Gene recombination": refers to the recombination of genes that control different traits. Modern genetic engineering technology implements genetic recombination in test tubes according to artificial design, also known as recombinant DNA. The purpose is to transfer the genetic gene in one individual cell to the DNA molecule in another individual cell with different traits to cause genetic variation. After target genes from a donor is transferred into a recipient bacterium, a gene product can be expressed to obtain products that are difficult to obtain by ordinary methods.

"Transformation" refers to cause cells or cultured recipient cells to obtain new genetic phenotypes by automatically obtaining or artificially supplying foreign DNA.

"Transduction" refers to transfer of DNA and recombination of genes occurring between a donor cell and a recipient cell when a virus is released from an infected (donor) cell and re-infects another (recipient) cell.

The term "prevention and/or treatment" when referring to FMDV infection refers to inhibition of replication and spread of FMDV or prevention of FMDV from colonizing its host, and alleviation of disease or symptoms of illness of the FMDV. If the viral load is reduced, the severity of the illness is reduced, and/or the food intake and/or growth are increased, then it can be considered that the treatment has achieved a therapeutic effect.

The description of the present disclosure is further provided as follows with reference to the specific embodiments, and features and advantages of the present disclosure will become more apparent from the following description. However, these embodiments are merely exemplary and do not limit the scope of the present disclosure in any way. It should be understood by a person skilled in the art that modifications or alternatives to details and forms of the technical solution of the present disclosure without deviation from the spirit and scope of the present disclosure will be allowed, while those modifications and alternatives should all fall within the scope of the present disclosure.

The chemical reagents used in the examples of the present disclosure are of analytical grade and are purchased from Sinopharm Group Co. Ltd. The experimental methods described in the present disclosure are conventional methods unless otherwise specified. The biological materials are commercially available unless otherwise specified.

Recombinant Vector pET28a-SUMOVP2-SUMOVP3-SUMOVP1 Containing VP2, VP3, VP1 Genes of Type a Foot and Mouth Disease Virus The type Afoot-and-mouth disease virus VP2 gene fragment shown in SEQ ID NO.1 in the sequence listing, the type A foot-and-mouth disease virus VP3 gene fragment shown in SEQ ID NO.2 in the sequence listing, and the type Afoot-and-mouth disease virus VP1 gene shown in SEQ ID NO.3 in the sequence listing were synthesized by GENEWIZ, Inc. and respectively ligated with pETSUMO vector. And then the successfully ligated recombinant plasmid was used as a template to amplify the fragments containing RBS-SUMO-VP2, T7-RBS-SUMO-VP3 and T7-RBS-SUMO-VP1. The fragments were digested with Xba I/BamH I, Sac I/Sal I, Not I/Xho I, and then cloned into the pET28a vector in sequence.

The ligation product was transformed into DH5a competent cells prepared with CaCl$_2$) which were then spread onto kanamycin-resistant solid LB medium. When single colonies were clearly visible, a single colony was picked into LB liquid medium containing kanamycin, and cultured at 230 rpm at 37° C. for 12 hours overnight, and the recombinant plasmid pET28a-SUMOVP2-SUMOVP3-SUMOVP1 was extracted.

The above-mentioned recombinant plasmid pET28a-SUMOVP2-SUMOVP3-SUMOVP1 inserted with the VP2, VP3, VP1 genes of type A foot-and-mouth disease virus was transformed into 40 μl of competent *E. coli* BL21(DE3) prepared by the calcium chloride method, which then were spread onto kanamycin-resistant solid LB medium, let stand at 37° C. for 10-12 hours until single colonies were clearly visible; a single colony was picked into a test tube containing 4 ml of kanamycin-resistant liquid LB medium, incubated at 37° C. with shaking at 230 rpm for 12 hours, from which 1 ml of bacterial solution was lyophilized and stored at −80° C.

Recombinant Vector Containing VP4, VP2, VP3, and VP1 Genes of Type O SEA Topotype Foot and Mouth Disease Virus The type O SEA topotype VP4 gene fragment shown in SEQ ID NO.4 in the sequence listing, the type O SEA topotype VP2 gene fragment shown in SEQ ID NO. 5 in the sequence listing, and the type O SEA topotype VP3 gene shown in SEQ ID NO. 6 in the sequence listing and the type O SEA topotype VP1 gene fragment shown in SEQ ID NO. 7 in the sequence listing were synthesized by GENEWIZ, Inc. and a *Escherichia coli* expression strain which contains recombinant plasmid pET28a-SUMOVP4-SUMOVP2-SUMOVP3-SUMOVP1 and can express tandemly VP4, VP2, VP3, and VP1 genes of type O SEA topotype foot-and-mouth disease virus was constructed. The strain was lyophilized and stored at −80° C.

Recombinant Vector Containing VP0, VP3, and VP1 Genes of Type O CATHAY Topotype Foot and Mouth Disease Virus The type O CATHAY topotype VP0 gene fragment shown in SEQ ID NO. 8 in the sequence listing, the type O CATHAY topotype VP3 gene fragment shown in SEQ ID NO. 9 in the sequence listing, and the type O CATHAY topotype VP1 gene shown in SEQ ID NO. 10 in the sequence listing were synthesized by GENEWIZ, Inc. and a *Escherichia coli* expression strain which contains recombinant plasmid pET28a-SUMOVP0-SUMOVP3-SUMOVP1 and can express tandemly VP0, VP3, and VP1 genes of type O CATHAY topotype foot-and-mouth disease virus was constructed. The strain was lyophilized and stored at −80° C.

Expression, Purification and Assembly of Antigen Proteins and Identification of Foot-and-Mouth Disease Virus-Like Particles (VLP)

Type A Foot-and-Mouth Disease Virus Antigen and VLP Particles

The *Escherichia coli* strain with recombinant plasmid pET28a-SUMOVP2-SUMOVP3-SUMOVP1 were taken out from −80° C., inoculated into 50 ml LB liquid medium resistant to kanamycin, cultured at 37° C. with shaking at 230 rpm for 12 hours, then transferred to 1 L LB liquid medium and cultivated at 37° C. to prepare seed broth for fermentation.

The fermentation tank is a 50 L fermentation tank (Shanghai Baoxing Bio-Engineer Equipment Co., Ltd.). 30 L of culture medium was prepared and put into the fermentation tank, sterilized at 121° C. for 30 minutes. On the next day, 3 L of seed broth was introduced to the fermentation tank, and when the concentration of cell culture reached about 10 OD600, the culture temperature was lowered to 25° C., and IPTG was added to a final concentration of 0.5 mM to induce cultivation for 12 hours. When the fermentation density was about 40 (OD600), the cultivation was stopped and the bacteria was collected by centrifugation.

The bacteria was resuspended, and broken 4 times at a pressure of 800 bar by using a homogenizer, which was then centrifuged at 13500 rpm for 40 min. The supernatant was retained and detected by 15% SDS-PAGE electrophoresis. The protein was roughly purified by ammonium sulfate fractional precipitation, followed by chromatographic purification, enzyme digestion, chromatographic purification to remove the SUMO fusion tag and assembly of type A foot-and-mouth disease virus-like particles. The purified protein was subjected to SDS-PAGE electrophoresis.

The type A foot-and-mouth disease virus-like particles were observed through the electron microscope after negative staining with phosphotungstic acid.

Type O SEA Topotype Foot-and-Mouth Disease Virus-Like Particle Antigen and VLP Particles The *E. coli* strain with recombinant plasmid pET28a-SUMOVP4-SUMOVP2-SUMOVP3-SUMOVP1 was taken out from −80° C. and inoculated into 50 ml LB liquid medium resistant to kanamycin, cultured according to the preparation conditions similar to that of the above-mentioned type A foot-and-mouth disease virus antigen, and then transferred to 1 L LB liquid medium and cultured at 37° C.

Using a 50 L fermentor, large-scale fermentation and expression of type O SEA topotype foot-and-mouth disease virus antigen were carried out according to the preparation conditions similar to that of the above-mentioned type A foot-and-mouth disease virus antigen.

The four type O SEA topotype foot-and-mouth disease virus antigens expressed in tandem in the bacteria were separated, purified and identified according to the preparation conditions similar to that of the above-mentioned type A foot-and-mouth disease virus antigen.

The type O SEA topotype foot-and-mouth disease virus-like particles were observed through the electron microscope after negative staining with phosphotungstic acid.

Type O CATHAY Topotype Foot-and-Mouth Disease Virus Antigen and VLP Particles

The *Escherichia coli* strain with recombinant plasmid pET28a-SUMOVP0-SUMOVP3-SUMOVP1 were taken out from −80° C., inoculated into 50 ml LB liquid medium resistant to kanamycin, cultured according to the preparation conditions similar to that of the above-mentioned type A foot-and-mouth disease virus antigen, then transferred to 1 L LB liquid medium and cultivated at 37° C.

Using a 50 L fermentor, large-scale fermentation and expression of type O CATHAY topotype foot-and-mouth disease virus antigen were carried out according to the preparation conditions similar to that of the above-mentioned type A foot-and-mouth disease virus antigen.

The three type O CATHAY topotype foot-and-mouth disease virus antigens expressed in tandem in the bacteria were separated, purified and identified according to the preparation conditions similar to that of the above-mentioned type A foot-and-mouth disease virus antigen.

The type O CATHAY topotype foot-and-mouth disease virus-like particles were observed through the electron microscope after negative staining with phosphotungstic acid.

Preparation of Foot-and-Mouth Disease Virus-Like Particle Vaccine Compositions

Vaccine Compositions Containing Type a Foot-and-Mouth Disease Virus-Like Particle Antigen The prepared type A foot-and-mouth disease virus-like particle antigen was taken and slowly added to an adjuvant, which was continuously stirred by an emulsifier at 800 rpm for 12 minutes during the process of adding, mixed well and stored at 4° C. Vaccine compositions containing type A foot-and-mouth disease virus-like particle antigen were prepared. Adjuvants suitable for use in the present disclosure may be adjuvants known to those skilled in the art. In the present disclosure, a biphasic adjuvant (water-in-oil-in-water emulsion), for example adjuvant ISA 206 (SEPPIC, France) is selected.

Vaccine Compositions Containing Type a Foot-and-Mouth Disease Virus-Like Particle Antigen and Type O SEA Topotype Foot-and-Mouth Disease Virus-Like Particle Antigen The prepared type A foot-and-mouth disease virus-like particle antigen as well as the prepared type O SEA topotype foot-and-mouth disease virus-like particle antigen were prepared according to the above method of preparing a vaccine composition containing type A foot-and-mouth disease virus-like particle antigen. Adjuvants suitable for use in the present disclosure may be adjuvants known to those skilled in the art. In the present disclosure, a biphasic adjuvant (water-in-oil-in-water emulsion), for example adjuvant ISA 206 (SEPPIC, France) is selected.

Vaccine Compositions Containing Type a Foot-and-Mouth Disease Virus-Like Particle Antigen, Type O SEA Topotype Foot-and-Mouth Disease Virus-Like Particle Antigen, and Type O CATHAY Topotype Foot-and-Mouth Disease Virus-Like Particle Antigen.

The prepared type Afoot-and-mouth disease virus-like particle antigen, type O SEA topotype foot-and-mouth disease virus-like particle antigen as well as type O CATHAY topotype foot-and-mouth disease virus-like particle antigen were prepared according to the above method of preparing a vaccine composition containing type A foot-and-mouth disease virus-like particle antigen. Adjuvants suitable for use in the present disclosure may be adjuvants known to those skilled in the art. In the present disclosure, a biphasic adjuvant (water-in-oil-in-water emulsion), for example adjuvant ISA 206 (SEPPIC, France) is selected.

Immunogenicity Analysis of Type a Foot-and-Mouth Disease Virus-Like Particle Vaccine Compositions Immunogenicity of Type Afoot-and-Mouth Disease Virus-Like Particle Vaccine Composition The immunogenicity of the antigen in the vaccine composition was measured with the level of the antibodies in immunized pigs' serum detected by ELISA.

Healthy and susceptible feeder pigs negative for type A FMDV antibody and antigen with a weight of about 40 kg were selected and immunized with a vaccine composition containing type A foot-and-mouth disease virus-like particle antigen. The immunization route of the immunization groups was intramuscular neck injection of 2 ml of vaccine, and the blank control group was immunized with the same amount of PBS. Blood samples were collected from each pig before immunization, and on the $7^{th}$, $14^{th}$, $21^{st}$, and $28^{th}$ days after immunization. A type A foot-and-mouth disease antibody ELISA test kit was used for antibody detection on the collected serum.

Duration Test of Immunity of Type a Foot-and-Mouth Disease Virus-Like Particle Vaccine Composition The duration of immunity of the antigen in the vaccine composition was measured with the level of the antibodies in the immunized pigs' serum detected by ELISA.

Healthy and susceptible feeder pigs negative for type A FMDV antibody and antigen with a weight of about 40 kg were selected and immunized with a vaccine composition containing type A foot-and-mouth disease virus-like particle antigen. The immunization route of the immunization groups was intramuscular neck injection of 2 ml of vaccine, and the blank control group was immunized with the same amount of PBS. All pigs were immunized once. Blood samples were collected from each pig before immunization, and on the $21^{st}$, $28^{th}$, $35^{th}$, $77^{th}$, $105^{th}$ and $133^{th}$ days after immunization.

An immunization group for a commercial inactivated vaccine (Re-O/MYA98/JSCZ/2013 strain+Re-A/WH/09 strain) was a control group. The immunization route was intramuscular neck injection of 2 ml of vaccine, and the blank control group was immunized with the same amount of PBS. Before immunization a blood sample was taken from each of the pigs, and on the $21^{st}$ day after 1st immunization a blood sample was taken and the 2nd immunization was made. On the $7^{th}$, $14^{th}$, $56^{th}$, $84^{th}$ and $112^{th}$ day after 2nd immunization, a blood sample was taken from each of the pigs.

Immunogenicity of Vaccine Compositions of Type a Foot-and-Mouth Disease Virus-Like Particle Antigen and Type O SEA Topotype Foot-and-Mouth Disease Virus-Like Particle Antigen The immunogenicity of the antigen in the vaccine composition was measured with the level of the antibodies in the immunized pigs' serum detected by ELISA.

Healthy and susceptible feeder pigs negative for type A and type O FMDV antibody and antigen with a weight of about 40 kg were selected and immunized with a prepared vaccine composition containing type A foot-and-mouth disease virus-like particle antigen and type O SEA topotype foot-and-mouth disease virus-like particle antigen, of which the immunization route was intramuscular neck injection of 2 ml of vaccine, and the blank control group was immunized with 2 ml of PBS. Blood samples were collected from each pig before immunization, and on the $7^{th}$, $14^{th}$, $21^{st}$, and $28^{th}$ days after immunization.

Immunogenicity of Vaccine Compositions of Type a Foot-and-Mouth Disease Virus-Like Particle Antigen, Type O SEA Topotype Foot-and-Mouth Disease Virus-Like Particle Antigen and Type O CATHAY Topotype Foot-and-Mouth Disease Virus-Like Particle Antigen The immunogenicity of the antigen in the vaccine composition was measured with the level of the antibodies in the immunized pigs' serum detected by ELISA.

Healthy and susceptible feeder pigs negative for type A and type O FMDV antibody and antigen with a weight of about 40 kg were selected and immunized with a prepared vaccine composition containing type A foot-and-mouth disease virus-like particle antigen, type O SEA topotype foot-and-mouth disease virus-like particle antigen and type O CATHAY topotype foot-and-mouth disease virus-like particle antigen, of which the immunization route was intramuscular neck injection of 2 ml of vaccine, and the control group was immunized with the vaccine composition containing type O SEA topotype foot-and-mouth disease virus-like particle antigen or type O CATHAY topotype foot-and-mouth disease virus-like particle antigen, the immunization route was intramuscular neck injection of 2 ml of vaccine and the blank control group was immunized with 2 ml of PBS. Blood samples were collected from each pig before immunization, and on the $7^{th}$, $14^{th}$, $21^{st}$, and $28^{th}$ days after immunization.

Example 1 Type A Foot-and-Mouth Disease Virus-Like Particles

The bacterial cells expressing type A foot-and-mouth disease virus antigen proteins were resuspended and as detected by SDS-PAGE electrophoresis, it showed that the three target proteins expressed in tandem in the supernatant were expressed. As detected by the SDS-PAGE electrophoresis for the purified proteins, it showed that the target proteins were all purified and enriched.

It can be observed through the electron microscope after negative staining with phosphotungstic acid that the type A FMDV protein has formed virus-like particles, and the formed virus-like particles are plump, with high assembly efficiency and no aggregation. After being placed at 4° C. for 3 months, it can be observed through the electron microscope after negative staining with phosphotungstic acid that the virus-like particles are still plump without aggregation. It shows that the foot-and-mouth disease protein prepared by the sequence screened by the present disclosure forms stable virus-like particles.

Example 2 Preparation of a Vaccine Composition of Type a Foot-and-Mouth Disease Virus-Like Particle Specific ratio of each component in the prepared vaccine is shown in Table 1.

TABLE 1

Component ratio of vaccine compositions of type A foot-and-mouth disease virus-like particle

| Component | Vaccine 1 | Vaccine 2 | Vaccine 3 |
|---|---|---|---|
| FMDV antigen (µg/ml) | 160 | 200 | 240 |
| Biphasic adjuvant (V/V %) | 50% | 50% | 50% |

Example 3 Immunogenicity Test of Vaccine Compositions Containing Type a Foot-and-Mouth Disease Virus-Like Particle Antigen 20 healthy and susceptible feeder pigs negative for type A FMDV antibody and antigen with a weight of about 40 kg were selected and randomly divided into 5 groups, 4 pigs per group. Groups 1-3 were immunization groups for corresponding vaccine 1, vaccine 2, and vaccine 3 prepared by Example 2 of the present disclosure, respectively, and group 4 is a blank control group. The immunization route of the immunization group was intramuscular neck injection of 2 ml of vaccine, and the control group was immunized with the same amount of PBS.

The antibody titer results showed that the antibodies of all pigs were negative before immunization with vaccines which could reach above 1:128 on the $14^{th}$ day after the first immunization. The antibody of the blank control group was negative and there was no change. The specific results are shown in Table 2.

TABLE 2

Antibody levels of type A foot-and-mouth disease virus detected by ELISA

| Group | Pig No. | Before immuni-zation | Day 7 after immuni-zation | Day 14 after immuni-zation | Day 21 after immuni-zation | Day 28 after immuni-zation |
|---|---|---|---|---|---|---|
| 1 | 1 | <1:8 | 1:64 | 1:128 | 1:360 | 1:720 |
|   | 2 | <1:8 | 1:45 | 1:128 | 1:360 | 1:360 |
|   | 3 | <1:8 | 1:64 | 1:128 | 1:360 | 1:360 |
|   | 4 | <1:8 | 1:64 | 1:128 | 1:360 | 1:720 |
|   | 5 | <1:8 | 1:64 | 1:128 | 1:360 | 1:360 |
| 2 | 6 | <1:8 | 1:64 | 1:128 | 1:360 | 1:360 |
|   | 7 | <1:8 | 1:64 | 1:128 | 1:360 | 1:720 |
|   | 8 | <1:8 | 1:64 | 1:180 | 1:720 | 1:720 |
|   | 9 | <1:8 | 1:64 | 1:128 | 1:360 | 1:720 |
|   | 10 | <1:8 | 1:64 | 1:128 | 1:360 | 1:360 |
| 3 | 11 | <1:8 | 1:90 | 1:180 | 1:720 | 1:720 |
|   | 12 | <1:8 | 1:64 | 1:180 | 1:360 | 1:360 |
|   | 13 | <1:8 | 1:64 | 1:128 | 1:360 | 1:360 |
|   | 14 | <1:8 | 1:64 | 1:180 | 1:720 | 1:720 |
|   | 15 | <1:8 | 1:64 | 1:128 | 1:360 | 1:720 |
| 4 | 16 | <1:8 | <1:8 | <1:8 | <1:8 | <1:8 |
|   | 17 | <1:8 | <1:8 | <1:8 | <1:8 | <1:8 |
|   | 18 | <1:8 | <1:8 | <1:8 | <1:8 | <1:8 |
|   | 19 | <1:8 | <1:8 | <1:8 | <1:8 | <1:8 |
|   | 20 | <1:8 | <1:8 | <1:8 | <1:8 | <1:8 |

It shows that the virus-like particles prepared by the present disclosure can quickly form high levels of specific antibodies, and can provide excellent immune protection against type A foot-and-mouth disease on the $14^{th}$ day after immunization even when the antigen content is only 160 µg/ml.

Example 4 Comparative Test of the Duration of Immunity of Vaccine Compositions Containing Type a Foot-and-Mouth Disease Virus-Like Particle Antigen 20 healthy and susceptible feeder pigs negative for type A FMDV antibody and antigen with a weight of about 40 kg were selected and randomly divided into 5 groups, 4 pigs per group. Group 5 was an immunization group for vaccine 2 prepared by Example 2 of the present disclosure, group 7 was an immunization group for a commercial inactivated vaccine (Re-O/MYA98/JSCZ/2013 strain+Re-A/WH/09 strain) and groups 6 and 8 were blank control groups. The immunization route of group 5 as the immunization group was intramuscular neck injection of 2 ml of vaccine, and group 6 as the control group was immunized with the same amount of PBS; all pigs were immunized once and a blood sample was taken from each of the pigs before immunization, and on the $21^{st}$, $28^{th}$, $35^{th}$, $77^{th}$, $105^{th}$, and $133^{th}$ days after immunization. The immunization route of group 7 was intramuscular neck injection of 2 ml, and group 8 as the control group was immunized with the same amount of PBS; blood was collected from each pig before immunization and on the 21st day after immunizations of groups 7 and 8, followed by 2nd immunization; on the $7^{th}$, $14^{th}$, $56^{th}$, $84^{th}$ and $112^{th}$ day after 2nd immunization, a blood sample was taken from each of the pigs.

The results showed that the antibodies of all pigs were negative before vaccination. On the $21^{st}$ day after the first immunization, the antibodies of the immunization group for vaccine 2 can reach above 1:128, and the antibodies of the immunization group for commercial vaccine cannot reach 1:128, which can only reach 1:128 on the $7^{th}$ day after the second immunization; the immunization group for vaccine 2 can still maintain a relatively high antibody level on the 133rd day after the first immunization, and antibody levels detected by ELISA can reach above 1:180, while some pigs of the immunization group for commercial vaccine had an antibody level close to a critical value of immune protection, 1:128 on the 112th day after the second immunization. The antibodies of the pigs in the control group were negative and there was no change. The specific results are shown in Table 3.

16 high assembly efficiency and no aggregation. After being placed at 4° C. for 3 months, it can be observed through the electron microscope after negative staining with phospho-tungstic acid that the FMD virus-like particles are still plump without aggregation. It shows that the foot-and-mouth disease protein prepared by the sequence screened by the present disclosure forms stable virus-like particles.

TABLE 3

Comparative result of antibody levels of type A
foot-and-mouth disease virus detected by ELISA

| Group | Pig No. | Before 1$^{st}$ immuni-zation | Day 21 after 1$^{st}$ immuni-zation | Day 28 after 1$^{st}$ immuni-zation | Day 35 after 1$^{st}$ immuni-zation | Day 77 after 1$^{st}$ immuni-zation | Day 105 after 1$^{st}$ immuni-zation | Day 133 after 1$^{st}$ immuni-zation |
|---|---|---|---|---|---|---|---|---|
| 5 | 21 | <1:8 | 1:360 | 1:360 | 1:720 | 1:360 | 1:360 | 1:180 |
|   | 22 | <1:8 | 1:360 | 1:360 | 1:720 | 1:720 | 1:360 | 1:180 |
|   | 23 | <1:8 | 1:360 | 1:720 | 1:720 | 1:360 | 1:360 | 1:180 |
|   | 24 | <1:8 | 1:720 | 1:720 | 1:720 | 1:720 | 1:360 | 1:360 |
|   | 25 | <1:8 | 1:360 | 1:720 | 1:720 | 1:720 | 1:360 | 1:360 |
| 6 | 26 | <1:8 | <1:8 | <1:8 | <1:8 | <1:8 | <1:8 | <1:8 |
|   | 27 | <1:8 | <1:8 | <1:8 | <1:8 | <1:8 | <1:8 | <1:8 |
|   | 28 | <1:8 | <1:8 | <1:8 | <1:8 | <1:8 | <1:8 | <1:8 |
|   | 29 | <1:8 | <1:8 | <1:8 | <1:8 | <1:8 | <1:8 | <1:8 |
|   | 30 | <1:8 | <1:8 | <1:8 | <1:8 | <1:8 | <1:8 | <1:8 |

| Group | Pig No. | Before 1$^{st}$ immuni-zation | Day 21 after 1$^{st}$ immuni-zation | Day 7 after 2$^{nd}$ immuni-zation | Day 14 after 2$^{nd}$ immuni-zation | Day 56 after 2$^{nd}$ immuni-zation | Day 84 after 2$^{nd}$ immuni-zation | Day 112 after 2$^{nd}$ immuni-zation |
|---|---|---|---|---|---|---|---|---|
| 7 | 31 | <1:8 | 1:45 | 1:360 | 1:720 | 1:720 | 1:360 | 1:180 |
|   | 32 | <1:8 | 1:45 | 1:180 | 1:360 | 1:360 | 1:180 | 1:180 |
|   | 33 | <1:8 | 1:45 | 1:360 | 1:720 | 1:360 | 1:180 | 1:128 |
|   | 34 | <1:8 | 1:45 | 1:180 | 1:360 | 1:360 | 1:180 | 1:128 |
|   | 35 | <1:8 | 1:45 | 1:180 | 1:360 | 1:360 | 1:180 | 1:128 |
| 8 | 36 | <1:8 | <1:8 | <1:8 | <1:8 | <1:8 | <1:8 | <1:8 |
|   | 37 | <1:8 | <1:8 | <1:8 | <1:8 | <1:8 | <1:8 | <1:8 |
|   | 38 | <1:8 | <1:8 | <1:8 | <1:8 | <1:8 | <1:8 | <1:8 |
|   | 39 | <1:8 | <1:8 | <1:8 | <1:8 | <1:8 | <1:8 | <1:8 |
|   | 40 | <1:8 | <1:8 | <1:8 | <1:8 | <1:8 | <1:8 | <1:8 |

The above experiments show that the virus-like particle vaccine composition prepared by the present disclosure, compared with the commercial inactivated whole-virus vaccine, not only can provide fast production of antibodies at a high level for the type A foot-and-mouth disease virus-like particle antigen, with an excellent immune protection effect after only a single-shot immunization, but also can significantly increase the duration of immunity and maintain immune protection for a longer time.

Example 5 Type O SEA Topotype Foot-and-Mouth
Disease Virus-Like Particles

The bacterial cells expressing type O SEA topotype foot-and-mouth disease virus protein antigens were resuspended and as detected by SDS-PAGE electrophoresis, it showed that the four target proteins expressed in tandem in the supernatant were expressed. The proteins after the purification was detected by the SDS-PAGE electrophoresis, showing that the target proteins were all purified and enriched.

It can be observed through the electron microscope after negative staining with phosphotungstic acid that the type O SEA topotype FMDV protein has formed virus-like particles, and the formed virus-like particles are plump, with Example 6 Preparation of Bivalent Vaccine
Compositions of Type O SEA Topotype and Type a
Foot-and-Mouth Disease Virus-Like Particles Specific ratio of each component in the prepared vaccine is shown in Table 4.

TABLE 4

Component ratios of bivalent vaccine compositions of type O SEA
topotype and type A foot-and-mouth disease virus-like particles

| Component | Vaccine 4 | Vaccine 5 | Vaccine 6 |
|---|---|---|---|
| Type A foot-and-mouth disease antigen (µg/ml) | 160 | 200 | 240 |
| Type O SEA topotype foot-and-mouth disease antigen (µg/ml) | 100 | 150 | 200 |
| Biphasic adjuvant (V/V %) | 50% | 50% | 50% |

Example 7 Immunogenicity Test of Bivalent
Vaccine Compositions of Type O SEA Topotype
and Type a Foot-and-Mouth Disease Virus-Like
Particles 20 healthy and susceptible feeder pigs negative for type A and type O FMDV antibody and antigen with a weight of about 40 kg were selected and randomly divided into 4 groups, 5 pigs per group. Groups 9-11 were immunization groups for corresponding vaccine 4, 5 and 6 prepared by Example 6 of the present disclosure respectively, and group 12 is a blank control group. The immunization route was intramuscular neck injection of 2 ml of vaccine, and the blank control group was immunized with 2 ml of PBS. Before immunization and on the 7th, 14th, 21st, and 28th day after immunization, a blood sample was taken from each of the pigs.

Use the type A Foot-and-Mouth Disease Antibody ELISA Test Kit to detect the relevant antibodies on the collected sera. The results showed that the antibodies of all pigs were negative before vaccination, which could all reach above 1:128 on the 14th day after a single-shot vaccination; the antibodies of the blank control group were negative and there was no change. The specific results are shown in Table 5.

TABLE 5

Antibody levels of type A foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| 9 | 41 | <1:8 | 1:64 | 1:128 | 1:360 | 1:360 |
| | 42 | <1:8 | 1:64 | 1:128 | 1:360 | 1:360 |
| | 43 | <1:8 | 1:45 | 1:128 | 1:360 | 1:360 |
| | 44 | <1:8 | 1:64 | 1:128 | 1:360 | 1:720 |
| | 45 | <1:8 | 1:64 | 1:128 | 1:360 | 1:720 |
| 10 | 46 | <1:8 | 1:64 | 1:128 | 1:360 | 1:720 |
| | 47 | <1:8 | 1:64 | 1:128 | 1:360 | 1:360 |
| | 48 | <1:8 | 1:64 | 1:180 | 1:720 | 1:720 |
| | 49 | <1:8 | 1:64 | 1:128 | 1:360 | 1:720 |
| | 50 | <1:8 | 1:64 | 1:128 | 1:360 | 1:360 |
| 11 | 51 | <1:8 | 1:90 | 1:180 | 1:720 | 1:720 |
| | 52 | <1:8 | 1:64 | 1:128 | 1:360 | 1:360 |
| | 53 | <1:8 | 1:64 | 1:180 | 1:720 | 1:720 |
| | 54 | <1:8 | 1:64 | 1:128 | 1:360 | 1:720 |
| | 55 | <1:8 | 1:64 | 1:128 | 1:360 | 1:360 |
| 12 | 56 | <1:8 | <1:8 | <1:8 | <1:8 | <1:8 |
| | 57 | <1:8 | <1:8 | <1:8 | <1:8 | <1:8 |
| | 58 | <1:8 | <1:8 | <1:8 | <1:8 | <1:8 |
| | 59 | <1:8 | <1:8 | <1:8 | <1:8 | <1:8 |
| | 60 | <1:8 | <1:8 | <1:8 | <1:8 | <1:8 |

A type O SEA topotype Foot-and-Mouth Disease Antibody ELISA Test Kit was used to detect the relevant antibodies on the collected sera. The results showed that the antibodies of all pigs of each immunization group were negative before vaccination, which could all reach above 1:128 on the 14th day after a single-shot vaccination; the antibody of the pigs of the blank control group was negative and there was no change. The specific results are shown in Table 6.

TABLE 6

Antibody levels of type O SEA topotype foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| 9 | 41 | <1:8 | 1:64 | 1:128 | 1:360 | 1:360 |
| | 42 | <1:8 | 1:64 | 1:180 | 1:720 | 1:720 |
| | 43 | <1:8 | 1:64 | 1:128 | 1:720 | 1:720 |
| | 44 | <1:8 | 1:64 | 1:128 | 1:360 | 1:360 |
| | 45 | <1:8 | 1:64 | 1:128 | 1:360 | 1:720 |
| 10 | 46 | <1:8 | 1:90 | 1:180 | 1:720 | 1:720 |
| | 47 | <1:8 | 1:64 | 1:128 | 1:360 | 1:360 |

TABLE 6-continued

Antibody levels of type O SEA topotype foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| | 48 | <1:8 | 1:64 | 1:128 | 1:360 | 1:720 |
| | 49 | <1:8 | 1:64 | 1:180 | 1:720 | 1:720 |
| | 50 | <1:8 | 1:90 | 1:180 | 1:720 | 1:720 |
| 11 | 51 | <1:8 | 1:64 | 1:180 | 1:720 | 1:720 |
| | 52 | <1:8 | 1:90 | 1:180 | 1:720 | 1:720 |
| | 53 | <1:8 | 1:90 | 1:180 | 1:720 | 1:720 |
| | 54 | <1:8 | 1:64 | 1:128 | 1:360 | 1:720 |
| | 55 | <1:8 | 1:90 | 1:180 | 1:720 | 1:720 |
| 12 | 56 | <1:8 | <1:8 | <1:8 | <1:8 | <1:8 |
| | 57 | <1:8 | <1:8 | <1:8 | <1:8 | <1:8 |
| | 58 | <1:8 | <1:8 | <1:8 | <1:8 | <1:8 |
| | 59 | <1:8 | <1:8 | <1:8 | <1:8 | <1:8 |
| | 60 | <1:8 | <1:8 | <1:8 | <1:8 | <1:8 |

The above experiments show that the vaccine compositions of type A and type O SEA topotype foot-and-mouth disease virus-like particles prepared by the present disclosure can quickly form high-level specific antibodies, and can provide good immune protection against type A and type O SEA topotype foot-and-mouth disease.

Example 8 Type O CATHAY Topotype Foot-and-Mouth Disease Virus-Like Particles

The bacterial cells expressing type O CATHAY topotype foot-and-mouth disease virus protein antigens were resuspended and as detected by SDS-PAGE electrophoresis, it showed that the three target proteins expressed in tandem in the supernatant were expressed. The proteins after purification were detected by the SDS-PAGE electrophoresis, showing that the target proteins were all purified and enriched.

It can be observed through the electron microscope after negative staining with phosphotungstic acid that the type O CATHAY topotype FMDV protein has formed virus-like particles, and the formed virus-like particles are plump, with high assembly efficiency and no aggregation. After being placed at 4° C. for 3 months, it can be observed through the electron microscope after negative staining with phosphotungstic acid that the FMD virus-like particles are still plump without aggregation. It shows that the foot-and-mouth disease protein prepared by the sequence screened by the present disclosure forms stable virus-like particles.

Example 9 Preparation of Bivalent Vaccine Compositions of Type O (SEA Topotype, CATHAY Topotype) and Type a Foot-and-Mouth Disease Virus-Like Particles Specific ratio of each component in the prepared vaccines is shown in Table 7.

TABLE 7

Component ratios of bivalent vaccine compositions of type O (SEA topotype, CATHAY topotype) and type A foot-and-mouth disease virus-like particles

| Component | Vaccine 7 | Vaccine 8 | Vaccine 9 | Vaccine 10 | Vaccine 11 |
|---|---|---|---|---|---|
| Type A foot-and-mouth disease antigen (μg/ml) | 160 | 200 | 240 | — | — |
| Type O SEA topotype foot-and-mouth disease antigen (μg/ml) | 100 | 150 | 200 | 200 | — |

TABLE 7-continued

Component ratios of bivalent vaccine compositions
of type O (SEA topotype, CATHAY topotype) and type
A foot-and-mouth disease virus-like particles

| Component | Vaccine 7 | Vaccine 8 | Vaccine 9 | Vaccine 10 | Vaccine 11 |
|---|---|---|---|---|---|
| Type O CATHAY topotype foot-and-mouth disease antigen (μg/ml) | 100 | 150 | 200 | — | 200 |
| Biphasic adjuvant (V/V %) | 50% | 50% | 50% | 50% | 50% |

Example 10 Immunogenicity Test of Bivalent Vaccine Compositions of Type O (SEA Topotype, CATHAY Topotype) and Type a Foot-and-Mouth Disease Virus-Like Particles 30 healthy and susceptible feeder pigs negative for type A and type O FMDV antibody and antigen with a weight of about 40 kg were selected and randomly divided into 6 groups, 5 pigs per group. Groups 13-15 were immunization groups for corresponding vaccines 7, 8, and 9 prepared by Example 9 of the present disclosure respectively and the immunization route was intramuscular neck injection of 2 ml; groups 16-17 were immunization groups for corresponding vaccines 10 and 11 prepared by Example 9 of the present disclosure respectively and the immunization route was intramuscular neck injection of 2 ml; group 18 is a blank control group and the immunization route was intramuscular neck injection of 2 ml of PBS. Before immunization and on the $7^{th}$, $14^{th}$, $21^{st}$, and $28^{th}$ day after immunization, a blood sample was taken/collected from each of the pigs.

The type A Foot-and-Mouth Disease Antibody ELISA Test Kit was used to detect the relevant antibodies on the collected sera. The results showed that the antibodies of all pigs were negative before vaccination, and antibodies of group 13, 14 and 15 could all reach above 1:128 on the $14^{th}$ day after a single-shot vaccination; the antibodies of groups 16 and 17 and the blank control group were negative and there was no change. The specific results are shown in Table 8.

TABLE 8

Antibody levels of type A foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| 13 | 61 | <1:8 | 1:45 | 1:128 | 1:360 | 1:360 |
| | 62 | <1:8 | 1:64 | 1:128 | 1:360 | 1:720 |
| | 63 | <1:8 | 1:45 | 1:128 | 1:360 | 1:360 |
| | 64 | <1:8 | 1:64 | 1:128 | 1:360 | 1:360 |
| | 65 | <1:8 | 1:64 | 1:128 | 1:360 | 1:720 |
| 14 | 66 | <1:8 | 1:64 | 1:180 | 1:720 | 1:720 |
| | 67 | <1:8 | 1:64 | 1:128 | 1:360 | 1:720 |
| | 68 | <1:8 | 1:45 | 1:128 | 1:360 | 1:360 |
| | 69 | <1:8 | 1:64 | 1:128 | 1:360 | 1:360 |
| | 70 | <1:8 | 1:64 | 1:128 | 1:360 | 1:720 |
| 15 | 71 | <1:8 | 1:64 | 1:180 | 1:720 | 1:720 |
| | 72 | <1:8 | 1:90 | 1:180 | 1:720 | 1:720 |
| | 73 | <1:8 | 1:64 | 1:128 | 1:360 | 1:360 |
| | 74 | <1:8 | 1:64 | 1:128 | 1:360 | 1:360 |
| | 75 | <1:8 | 1:64 | 1:128 | 1:360 | 1:720 |
| 16 | 76 | <1:8 | <1:8 | <1:8 | <1:8 | <1:8 |
| | 77 | <1:8 | <1:8 | <1:8 | <1:8 | <1:8 |
| | 78 | <1:8 | <1:8 | <1:8 | <1:8 | <1:8 |

TABLE 8-continued

Antibody levels of type A foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| | 79 | <1:8 | <1:8 | <1:8 | <1:8 | <1:8 |
| | 80 | <1:8 | <1:8 | <1:8 | <1:8 | <1:8 |
| 17 | 81 | <1:8 | <1:8 | <1:8 | <1:8 | <1:8 |
| | 82 | <1:8 | <1:8 | <1:8 | <1:8 | <1:8 |
| | 83 | <1:8 | <1:8 | <1:8 | <1:8 | <1:8 |
| | 84 | <1:8 | <1:8 | <1:8 | <1:8 | <1:8 |
| | 85 | <1:8 | <1:8 | <1:8 | <1:8 | <1:8 |
| 18 | 86 | <1:8 | <1:8 | <1:8 | <1:8 | <1:8 |
| | 87 | <1:8 | <1:8 | <1:8 | <1:8 | <1:8 |
| | 88 | <1:8 | <1:8 | <1:8 | <1:8 | <1:8 |
| | 89 | <1:8 | <1:8 | <1:8 | <1:8 | <1:8 |
| | 90 | <1:8 | <1:8 | <1:8 | <1:8 | <1:8 |

A type O SEA topotype Foot-and-Mouth Disease Antibody ELISA Test Kit was used to detect the relevant antibodies on the collected sera. The results showed that the antibodies of all pigs were negative before vaccination, and antibodies of group 13, 14, 15 and 16 could all reach above 1:128 on the $14^{th}$ day after a single-shot vaccination; as to the immunization group for the bivalent (three-component) foot-and-mouth disease virus-like particle vaccine composition at a low content, the antibody level still met or exceeded the antibody level of the immunization group with the monovalent type O SEA topotype foot-and-mouth disease virus-like particle vaccine composition at a high content; the antibodies of group 17 and the blank control group were negative and there was no change. The specific results are shown in Table 9. Comparing the ELISA test results of the type O SEA topotype foot-and-mouth disease antibodies in groups 13, 14, 15 and 16, in the bivalent vaccine composition of the type O (SEA, CATHAY) and type A foot-and-mouth disease virus-like particles of the present disclosure, a synergistic effect is produced between the two O-type antigens, so that the immune effect can still be guaranteed even when the content of type O SEA topotype foot-and-mouth disease virus-like particle antigen was reduced by half.

TABLE 9

Antibody levels of type O SEA topotype foot-and-mouth disease virus detected by ELISA

| Group | Pig No. | Before immuni- zation | Day 7 after immuni- zation | Day 14 after immuni- zation | Day 21 after immuni- zation | Day 28 after immuni- zation |
|---|---|---|---|---|---|---|
| 13 | 61 | <1:8 | 1:90 | 1:180 | 1:720 | 1:720 |
| | 62 | <1:8 | 1:64 | 1:128 | 1:360 | 1:360 |
| | 63 | <1:8 | 1:90 | 1:180 | 1:720 | 1:720 |
| | 64 | <1:8 | 1:64 | 1:180 | 1:720 | 1:720 |
| | 65 | <1:8 | 1:64 | 1:128 | 1:360 | 1:720 |
| 14 | 66 | <1:8 | 1:90 | 1:180 | 1:720 | 1:720 |
| | 67 | <1:8 | 1:90 | 1:180 | 1:720 | 1:720 |
| | 68 | <1:8 | 1:64 | 1:180 | 1:720 | 1:720 |
| | 69 | <1:8 | 1:90 | 1:180 | 1:720 | 1:720 |
| | 70 | <1:8 | 1:64 | 1:128 | 1:360 | 1:720 |
| 15 | 71 | <1:8 | 1:64 | 1:180 | 1:720 | 1:720 |
| | 72 | <1:8 | 1:90 | 1:180 | 1:720 | 1:720 |
| | 73 | <1:8 | 1:64 | 1:128 | 1:360 | 1:720 |
| | 74 | <1:8 | 1:90 | 1:180 | 1:720 | 1:720 |
| | 75 | <1:8 | 1:90 | 1:180 | 1:720 | 1:720 |
| 16 | 76 | <1:8 | 1:64 | 1:128 | 1:360 | 1:720 |
| | 77 | <1:8 | 1:90 | 1:180 | 1:720 | 1:720 |
| | 78 | <1:8 | 1:64 | 1:128 | 1:360 | 1:360 |
| | 79 | <1:8 | 1:64 | 1:180 | 1:720 | 1:720 |

TABLE 9-continued

Antibody levels of type O SEA topotype foot-and-mouth disease virus detected by ELISA

| Group | Pig No. | Before immuni-zation | Day 7 after immuni-zation | Day 14 after immuni-zation | Day 21 after immuni-zation | Day 28 after immuni-zation |
|---|---|---|---|---|---|---|
| | 80 | <1:8 | 1:90 | 1:180 | 1:720 | 1:720 |
| 17 | 81 | <1:8 | <1:8 | <1:8 | <1:8 | <1:8 |
| | 82 | <1:8 | <1:8 | <1:8 | <1:8 | <1:8 |
| | 83 | <1:8 | <1:8 | <1:8 | <1:8 | <1:8 |
| | 84 | <1:8 | <1:8 | <1:8 | <1:8 | <1:8 |
| | 85 | <1:8 | <1:8 | <1:8 | <1:8 | <1:8 |
| 18 | 86 | <1:8 | <1:8 | <1:8 | <1:8 | <1:8 |
| | 87 | <1:8 | <1:8 | <1:8 | <1:8 | <1:8 |
| | 88 | <1:8 | <1:8 | <1:8 | <1:8 | <1:8 |
| | 89 | <1:8 | <1:8 | <1:8 | <1:8 | <1:8 |
| | 90 | <1:8 | <1:8 | <1:8 | <1:8 | <1:8 |

A type O CATHAY topotype Foot-and-Mouth Disease Antibody ELISA Test Kit was used to detect the relevant antibodies on the collected sera. The results showed that the antibodies of all pigs were negative before vaccination, and antibodies of group 13, 14, 15 and 17 could all reach above 1:128 on the 14$^{th}$ day after a single-shot vaccination; after immunization with the bivalent (three-component) foot-and-mouth disease virus-like particle vaccine composition at a low content, the antibody level still met or exceeded the antibody level of the immunization group for the monovalent type O CATHAY topotype foot-and-mouth disease virus-like particle vaccine composition at a high content; the antibodies of group 16 and the blank control group were negative and there was no change. The specific results are shown in Table 10. Comparing the ELISA test results of the type O CATHAY topotype foot-and-mouth disease antibodies in groups 13, 14, 15 and 17, in the bivalent vaccine composition of the type O (SEA topotype, CATHAY topotype) and type A foot-and-mouth disease virus-like particles of the present disclosure, a synergistic effect is produced between the two O-type antigens, so that the immune effect can still be guaranteed even when the content of type O CATHAY topotype foot-and-mouth disease virus-like particle antigen was reduced by half.

TABLE 10

Antibody levels of type O CATHAY topotype foot-and-mouth disease virus detected by ELISA

| Group | Pig No. | Before immuni-zation | Day 7 after immuni-zation | Day 14 after immuni-zation | Day 21 after immuni-zation | Day 28 after immuni-zation |
|---|---|---|---|---|---|---|
| 13 | 61 | <1:8 | 1:64 | 1:128 | 1:360 | 1:360 |
| | 62 | <1:8 | 1:64 | 1:180 | 1:720 | 1:720 |
| | 63 | <1:8 | 1:64 | 1:128 | 1:360 | 1:720 |
| | 64 | <1:8 | 1:90 | 1:180 | 1:720 | 1:720 |
| | 65 | <1:8 | 1:64 | 1:128 | 1:360 | 1:720 |
| 14 | 66 | <1:8 | 1:64 | 1:180 | 1:720 | 1:720 |
| | 67 | <1:8 | 1:90 | 1:180 | 1:720 | 1:720 |
| | 68 | <1:8 | 1:64 | 1:128 | 1:360 | 1:720 |
| | 69 | <1:8 | 1:90 | 1:180 | 1:720 | 1:720 |
| | 70 | <1:8 | 1:64 | 1:128 | 1:360 | 1:720 |
| 15 | 71 | <1:8 | 1:64 | 1:128 | 1:360 | 1:720 |
| | 72 | <1:8 | 1:90 | 1:180 | 1:720 | 1:720 |
| | 73 | <1:8 | 1:90 | 1:180 | 1:720 | 1:720 |
| | 74 | <1:8 | 1:64 | 1:128 | 1:360 | 1:720 |
| | 75 | <1:8 | 1:90 | 1:180 | 1:720 | 1:720 |
| 16 | 76 | <1:8 | <1:8 | <1:8 | <1:8 | <1:8 |
| | 77 | <1:8 | <1:8 | <1:8 | <1:8 | <1:8 |
| | 78 | <1:8 | <1:8 | <1:8 | <1:8 | <1:8 |

TABLE 10-continued

Antibody levels of type O CATHAY topotype foot-and-mouth disease virus detected by ELISA

| Group | Pig No. | Before immuni-zation | Day 7 after immuni-zation | Day 14 after immuni-zation | Day 21 after immuni-zation | Day 28 after immuni-zation |
|---|---|---|---|---|---|---|
| | 79 | <1:8 | <1:8 | <1:8 | <1:8 | <1:8 |
| | 80 | <1:8 | <1:8 | <1:8 | <1:8 | <1:8 |
| 17 | 81 | <1:8 | 1:64 | 1:128 | 1:360 | 1:720 |
| | 82 | <1:8 | 1:64 | 1:128 | 1:360 | 1:720 |
| | 83 | <1:8 | 1:90 | 1:180 | 1:720 | 1:720 |
| | 84 | <1:8 | 1:64 | 1:180 | 1:720 | 1:720 |
| | 85 | <1:8 | 1:64 | 1:128 | 1:360 | 1:360 |
| 18 | 86 | <1:8 | <1:8 | <1:8 | <1:8 | <1:8 |
| | 87 | <1:8 | <1:8 | <1:8 | <1:8 | <1:8 |
| | 88 | <1:8 | <1:8 | <1:8 | <1:8 | <1:8 |
| | 89 | <1:8 | <1:8 | <1:8 | <1:8 | <1:8 |
| | 90 | <1:8 | <1:8 | <1:8 | <1:8 | <1:8 |

The above experiments show that the bivalent (three-component) foot-and-mouth disease virus-like particles prepared by the present disclosure can quickly form high-level specific antibodies, in which the two O-type antigens can synergize with each other, and can provide good immune protection against type O SEA topotype and CATHAY topotype foot-and-mouth disease even when the antigen content is reduced by half; at the same time, it also shows that monovalent type O CATHAY topotype foot-and-mouth disease virus-like particles can have a good immune response and achieve complete protection of pigs.

Example 11 Challenge Protection Test of Bivalent Vaccine Compositions of Type O (SEA Topotype, CATHAY Topotype) and Type a Foot-and-Mouth Disease Virus-Like Particles 34 healthy and susceptible feeder pigs negative for type A and type O FMDV antibody and antigen with a weight of about 40 kg were selected and randomly divided into 8 groups, 5 pigs per group for groups 19-23 and 3 pigs per group for groups 24-26. Groups 19-21 were immunization groups for corresponding vaccine 8 prepared by Example 9 of the present disclosure, and the immunization route was intramuscular neck injection of 2 ml of vaccine; groups 22-23 were immunization groups for commercial inactivated vaccine (Re-O/MYA98/JSCZ/2013 strain+ Re-A/WH/09 strain), and the immunization route was intramuscular neck injection of 2 ml of vaccine; and groups 24-26 are blank control groups, and the immunization route was intramuscular neck injection of 2 ml of PBS. The clinical symptoms of each group were observed after immunization. On the 28$^{th}$ day after vaccination, each pig was injected intramuscularly with 1000ID50 of virulent strains. The challenge strain used for groups 19, 22 and 24 was CATHAY topotype O/0718 strain, for groups 20, 23, and 25 was SEA topotype O/MYA98/BY/2010 strain, and for groups 21 and 26 was type A A/GDMM/2013 strain. After observation for 10 days, pigs with blisters or ulcers on at least one hoof are judged to have illness. The incidence and PD50 values are shown in Tables 11, 12 and 13.

TABLE 11

Challenge protection results of O/0718 strain

| Group | Immunization dose | Pig No. | Challenge protection results | PD50 |
|---|---|---|---|---|
| 19 | 2 ml/pig | 1419 | Protected | 15.59 |
| | | 1420 | protected | |
| | | 1423 | Protected | |
| | | 1425 | Protected | |
| | | 1426 | Protected | |
| 22 | 2 ml/pig | 1451 | Illness | 2.01 |
| | | 1454 | Illness | |
| | | 1455 | Protected | |
| | | 1457 | Protected | |
| | | 1458 | Illness | |
| 24 | 2 ml/pig | 1465 | Illness | — |
| | | 1482 | Illness | |
| | | 1484 | Illness | |

TABLE 12

Challenge protection results of O/MYA98/BY/2010 strain

| Group | Immunization dose | Pig No. | Challenge protection results | PD50 |
|---|---|---|---|---|
| 20 | 2 ml/pig | 1421 | Protected | 13.97 |
| | | 1422 | Protected | |
| | | 1424 | Protected | |
| | | 1427 | Protected | |
| | | 1428 | Protected | |
| 23 | 2 ml/pig | 1449 | Protected | 7.19 |
| | | 1450 | Protected | |
| | | 1452 | Illness | |
| | | 1453 | Protected | |
| | | 1456 | Protected | |
| 25 | 2 ml/pig | 1464 | Illness | — |
| | | 1466 | Illness | |
| | | 1483 | Illness | |

TABLE 13

Challenge protection results of A/GDMM/2013 strain

| Group | Immunization dose | Pig No. | Challenge protection results | PD50 |
|---|---|---|---|---|
| 21 | 2 ml/pig | A1 | Protected | 13.59 |
| | | A35 | Protected | |

TABLE 13-continued

Challenge protection results of A/GDMM/2013 strain

| Group | Immunization dose | Pig No. | Challenge protection results | PD50 |
|---|---|---|---|---|
| | | A41 | Protected | |
| | | A48 | Protected | |
| | | A77 | Protected | |
| 26 | 2 ml/pig | A24 | Illness | — |
| | | A70 | Illness | |
| | | A76 | Illness | |

The results show that the bivalent vaccine compositions of type O (SEA topotype, CATHAY topotype) and type A bivalent foot-and-mouth disease virus-like particles of the present disclosure can provide good immune protection effect against epidemic strains of type O SEA topotype and CATHAY topotype and type A foot-and-mouth disease, and the PD50 is 13.59-15.59; the commercial inactivated vaccine cannot fully protect against the type O SEA topotype foot-and-mouth disease epidemic strain, and the PD50 is 7.19; the commercial inactivated vaccine cannot effectively protect the type O CATHAY topotype foot-and-mouth disease epidemic strain, and the PD50 is 2.01.

It is shown that the bivalent vaccine compositions of type O (SEA topotype, CATHAY topotype) and type A foot-and-mouth disease virus-like particles of the present disclosure have good immunogenicity, can resist the attack of epidemic strains, and effectively address the problem that the existing inactivated vaccines cannot effectively protect against epidemic strains, and also have good biosafety.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art may make some equivalent variations or modifications to the above-disclosed technical content without departing from the scope of the technical solutions of the present disclosure to obtain equivalent examples. Without departing from the contents of the technical solutions of the present disclosure, any simple modifications, equivalent changes and modifications made to the above examples according to the technical essence of the present disclosure all fall within the scope of the technical solutions of the present disclosure.

The invention claimed is:

1. A type A foot-and-mouth disease virus-like particle antigen, wherein the type A foot-and-mouth virus-like particle antigen is assembled by VP2, VP3 and VP1 antigen proteins of an epidemic strain of type A foot-and-mouth disease virus, the type A foot-and-mouth disease virus VP2 antigen protein is encoded by a nucleotide sequence shown in SEQ ID No. 1 or its degenerate sequence, the type A foot-and-mouth disease virus VP3 antigen protein is encoded by a nucleotide sequence shown in SEQ ID No.
2 or its degenerate sequence, and the type A foot-and-mouth disease virus VP1 antigen protein is encoded by a nucleotide sequence shown in SEQ ID No. 3 or its degenerate sequence.

2. A vaccine composition, wherein the vaccine composition comprises an immune amount of the type A foot-and-mouth disease virus-like particle antigen according to claim 1 and a pharmaceutically acceptable carrier.

3. The vaccine composition according to claim 2, wherein content of the type A foot-and-mouth disease virus-like particle antigen is 160-240 µg/ml.

4. The vaccine composition according to claim 2, wherein the pharmaceutically acceptable carrier comprises an adjuvant which is selected from one or more of (1) mineral oil, alhydrogel adjuvant, saponins, Avridine, dimethyl-dioctadecyl-ammonium bromide (DDA); (2) water-in-oil emulsion, oil-in-water emulsion, water-in-oil-in-water emulsion; or (3) polymers of acrylic or methacrylic acid, copolymers of maleic anhydride and alkenyl derivative; and the RIBI adjuvant system, monophosphoryl lipid A, heat-labile enterotoxin from *E. coli*, cholera toxin, muramyl dipeptide; and content of the adjuvant is 5%-60% V/V.

5. The vaccine composition according to claim 2, wherein the vaccine composition further includes an immune amount of type O SEA topotype foot-and-mouth disease virus-like particle antigen and/or an immune amount of type O CATHAY topotype foot-and-mouth disease virus-like particle antigen, wherein the type O SEA topotype foot-and-mouth disease virus-like particle antigen is assembled by VP4, VP2, VP3 and VP1 antigen proteins of an epidemic strain of type O SEA topotype foot-and-mouth disease virus, wherein the type O SEA topotype foot-and-mouth disease virus VP4 antigen protein is encoded by a nucleotide sequence shown in SEQ ID No. 4 or its degenerate sequence, the type O SEA topotype foot-and-mouth disease virus VP2 antigen protein is encoded by a nucleotide sequence shown in SEQ ID No. 5 or its degenerate sequence, the type O SEA topotype foot-and-mouth disease virus VP3 antigen protein is encoded by a nucleotide sequence shown in SEQ ID No. 6 or its degenerate sequence, the type O SEA topotype foot-and-mouth disease virus VP1 antigen protein is encoded by a nucleotide sequence shown in SEQ ID No. 7 or its degenerate sequence; and the type O CATHAY topotype foot-and-mouth disease virus-like particle antigen is assembled by VP0, VP3 and VP1 antigen proteins of an epidemic strain of type O CATHAY topotype foot-and-mouth disease virus, wherein the type O CATHAY topotype foot-and-mouth disease virus VP0 antigen protein is encoded by a nucleotide sequence shown in SEQ ID No. 8 or its degenerate sequence, the type O CATHAY topotype foot-and-mouth disease virus VP3 antigen protein is encoded by a nucleotide sequence shown in SEQ ID No. 9 or its degenerate sequence, the type O CATHAY topotype foot-and-mouth disease virus VP1 antigen protein is encoded by a nucleotide sequence shown in SEQ ID No. 10 or its degenerate sequence.

6. The vaccine composition according to claim 5, wherein content of the type O SEA topotype foot-and-mouth disease virus-like particle antigen is 100-200 µg/ml; and content of the type O CATHAY topotype foot-and-mouth disease virus-like particle antigen is 100-200 µg/ml.

7. A method for preparing the vaccine composition according to claim 2, wherein the method comprises:

Step (1) cloning and recombining genes of VP2, VP3, VP1 antigen proteins of the type A foot-and-mouth disease virus respectively into a common tandem expression vector;

Step (2) transforming or transducing a host cell with the recombinant expression vector obtained in the step (1) and solubly expressing recombinant SUMO-VP2 antigen protein, recombinant SUMO-VP3 antigen protein and recombinant SUMO-VP1 antigen protein of type A foot-and-mouth disease virus which can self-assemble to form virus-like particle antigens;

Step (3) separating and purifying the recombinant antigens of type A foot-and-mouth disease virus obtained in the step (2) and removing SUMO fusion tags through digestion and purification; and step (4) self-assembling to form virus-like particle antigens, and adding an adjuvant to obtain the vaccine composition.

8. The method according to claim 7, wherein the tandem expression vector in step (1) is pET28a, pET28b or pET32a; the host cell in step (2) is *E. coli* BL21 (DE3), B(DE3) pLysS, or B(DE3).

9. The method according to claim 7, wherein in the step (2), after the host cell is amplified, Isopropyl-β-D-thiogalactoside (IPTG) is added to induce expression of the proteins.

10. Use of the vaccine composition according to claim 2 for preventing and/or treating type A foot-and-mouth disease, including a step of administering the vaccine composition to a subject in need.

11. The vaccine composition according to claim 3, wherein the content of the type A foot-and-mouth disease virus-like particle antigen is 160 µg/ml, 200 µg/ml or 240 µg/ml.

12. The vaccine composition according to claim 4, wherein the saponin is Quil A, QS-21 or GPI-0100, and the content of the adjuvant is 30%-60% V/V.

13. The vaccine composition according to claim 12, wherein the content of the adjuvant is 50% V/V.

14. The vaccine composition according to claim 6, wherein the content of the type O SEA topotype foot-and-mouth disease virus-like particle antigen is 100 µg/ml, 150 µg/ml, or 200 µg/ml, and the content of the type O CATHAY topotype foot-and-mouth disease virus-like particle antigen is 100 µg/ml, 150 µg/ml, or 200 µg/ml.

\* \* \* \* \*